US005129881A

United States Patent [19]

Pope

[11] Patent Number: 5,129,881

[45] Date of Patent: Jul. 14, 1992

[54] COUNTER-STRESSING TRACTION SYSTEM

[76] Inventor: Michael J. Pope, 1304 E. Main St., Troy, Ohio 45373

[21] Appl. No.: 761,399

[22] Filed: Sep. 18, 1991

[51] Int. Cl.[5] .................... A61F 5/00

[52] U.S. Cl. .................... 602/32; 606/241

[58] Field of Search .................... 602/32, 36, 39; 606/241, 242, 243, 244, 245

[56] References Cited

U.S. PATENT DOCUMENTS

| | | | |
|---|---|---|---|
| 2,593,675 | 4/1952 | Hastings et al. | 606/243 |
| 2,984,238 | 5/1961 | Axtell et al. | 602/32 |
| 3,403,675 | 10/1968 | Carr | 602/32 |
| 3,548,816 | 12/1970 | Bond | 602/32 |
| 3,750,658 | 8/1973 | Dawson, Jr. et al. | 602/32 |

*Primary Examiner*—Richard J. Apley
*Assistant Examiner*—Lynne A. Reichard
*Attorney, Agent, or Firm*—Jacox & Meckstroth

[57] ABSTRACT

A person's cervical spine is progressively remodeled to a normal anterior-posterior curve be seating the person on a chair in an upright position with a lumbar fulcrum pad located in the small of the person's back. An anterior fulcrum strap extends around the neck and is pulled forwardly and upwardly at a preselected angle and with a predetermined force to set the cervical or neck spine with a near normal or slightly forward curve. A headband extends around the person's forehead and the lower part of the skull, and a pair of stabilizer straps extend upwardly from the chair and pull the headband rearwardly with a predetermined force. The forces are applied to the straps by front and rear weights connected to the straps through cables extending around vertically adjustable pulleys. The weights are removable or lifted from the straps by power driven winches movable with a pulleys and controlled by the person.

18 Claims, 2 Drawing Sheets

COUNTER-STRESSING TRACTION SYSTEM

BACKGROUND OF THE INVENTION

In the art of traction devices or apparatus for correcting the curvature of the cervical spine of a human body for obtaining a normal anterior-posterior (AP) curve, there have been various devices either purposed or used, for example, the traction table disclosed in U.S. Pat. No. 4,951,654. As disclosed in this patent, a person reclines on a table, and a force is applied to a harness extending around the person's forehead in order to tilt the head rearwardly and downwardly over the top of the reclining table. There is also a device where the person lies horizontally on a table with a pad under the neck, and a weight pulls downwardly on the person's head by means of harness which extends around the person's chin and forehead. Another traction device involves pulling upwardly on the head of a standing person by means of a sling which extends under the person's chin and with the sling connected to a weight by a cable and pulley system supported by a bracket mounted on a door. Still another form of traction device is used with the person reclining slightly in a chair having a reclining back pad, and the person's head is tilted or pulled rearwardly by means of a harness attached to a weight behind the chair. The harness includes a band which extends over the person's forehead and is attached to a pair of straps which extend to the weight and also around the person's shoulders for attachment to the back of the chair.

SUMMARY OF THE INVENTION

The present invention is directed to an improved traction method and apparatus wherein a counter-stressing traction is used for returning the anterior to posterior lateral curves of a person's spine towards a normal curvature. In accordance with the present invention, the person is seated on a chair in an upright fashion with the buttocks pressed firmly against the back of the chair and with a lumbar fulcrum pillow placed in the small of the person's back in order to form or support the normal AP lateral curve. An anterior or front pulling fulcrum strap extends around the person's neck and is pulled forwardly and upwardly at a preselected angle with a force applying device in order to set the cervical spine of the neck into a nearly normal to a normally forward curve. A harness includes an adjustable headband which extends around the person's forehead and the occiput or lower back part of the skull. The sides of the headband are attached to a pair of stabilizing straps which extend forwardly and downwardly and are adjustably connected to front hook portions of the chair. The straps extend rearwardly or generally horizontally from the headband to another force applying device. Preferably, the forces applied to the fulcrum strap and the headband harness straps are produced by predetermined weights attached to cables extending around pulleys to the straps. The weights are removable or lifted from the straps under the control of the person by means of power operated winches having depending cables connected to the weights. The forward pulling or force applying device and the rearward pulling or force applying device are independently adjustable on corresponding vertical frame members in order to obtain the preferred angle and force application to each of the straps.

Other features and advantages of the invention will be apparent from the following description, the accompanying drawings and the appended claims.

DESCRIPTION OF THE PREFERRED EMBODIMENTS

Figure 1:
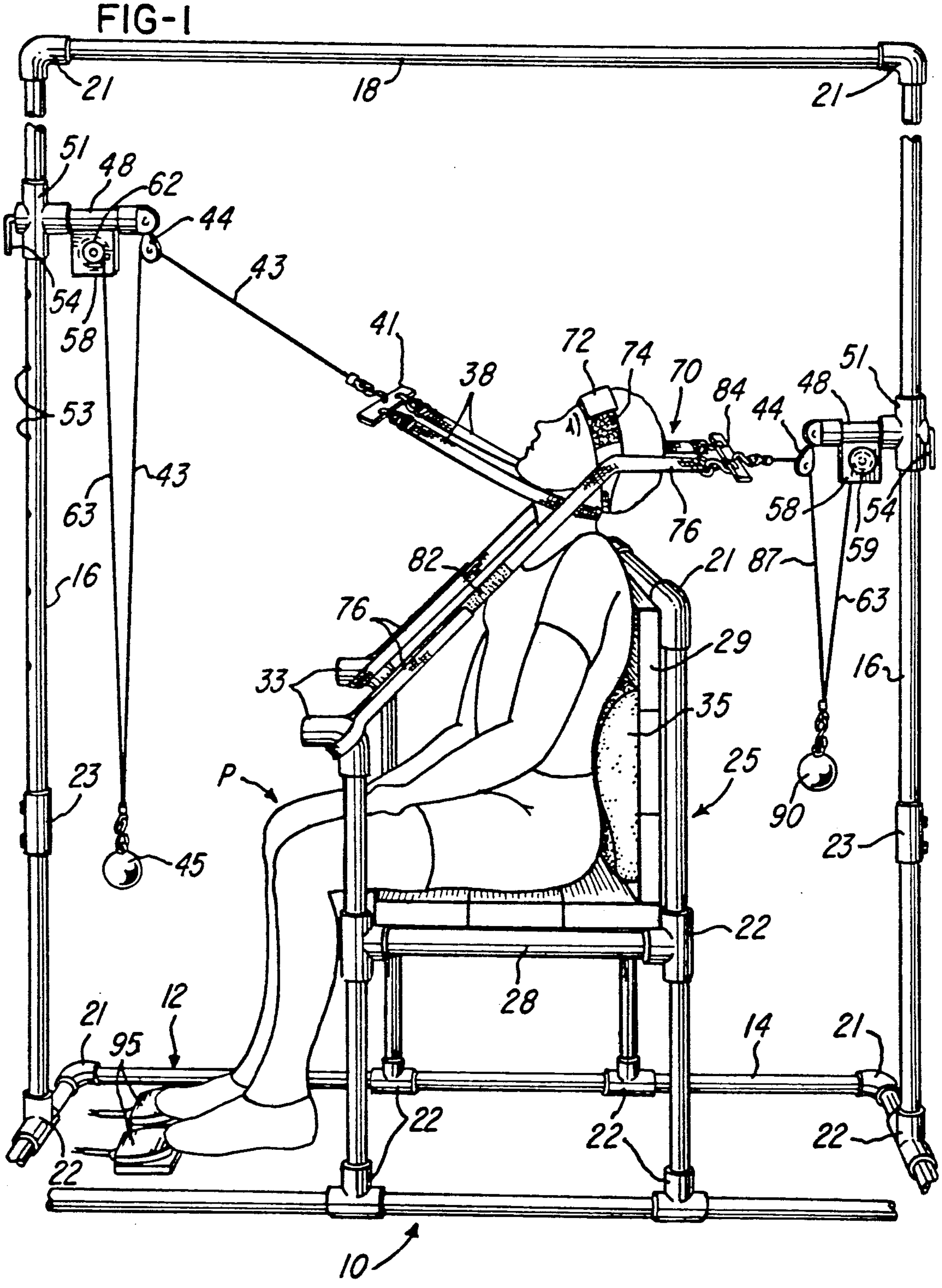
FIG. 1 is a side elevational view of apparatus constructed in accordance with the invention for obtaining a counter-stressing traction for correcting a person's cervical spine.
Figure 2:
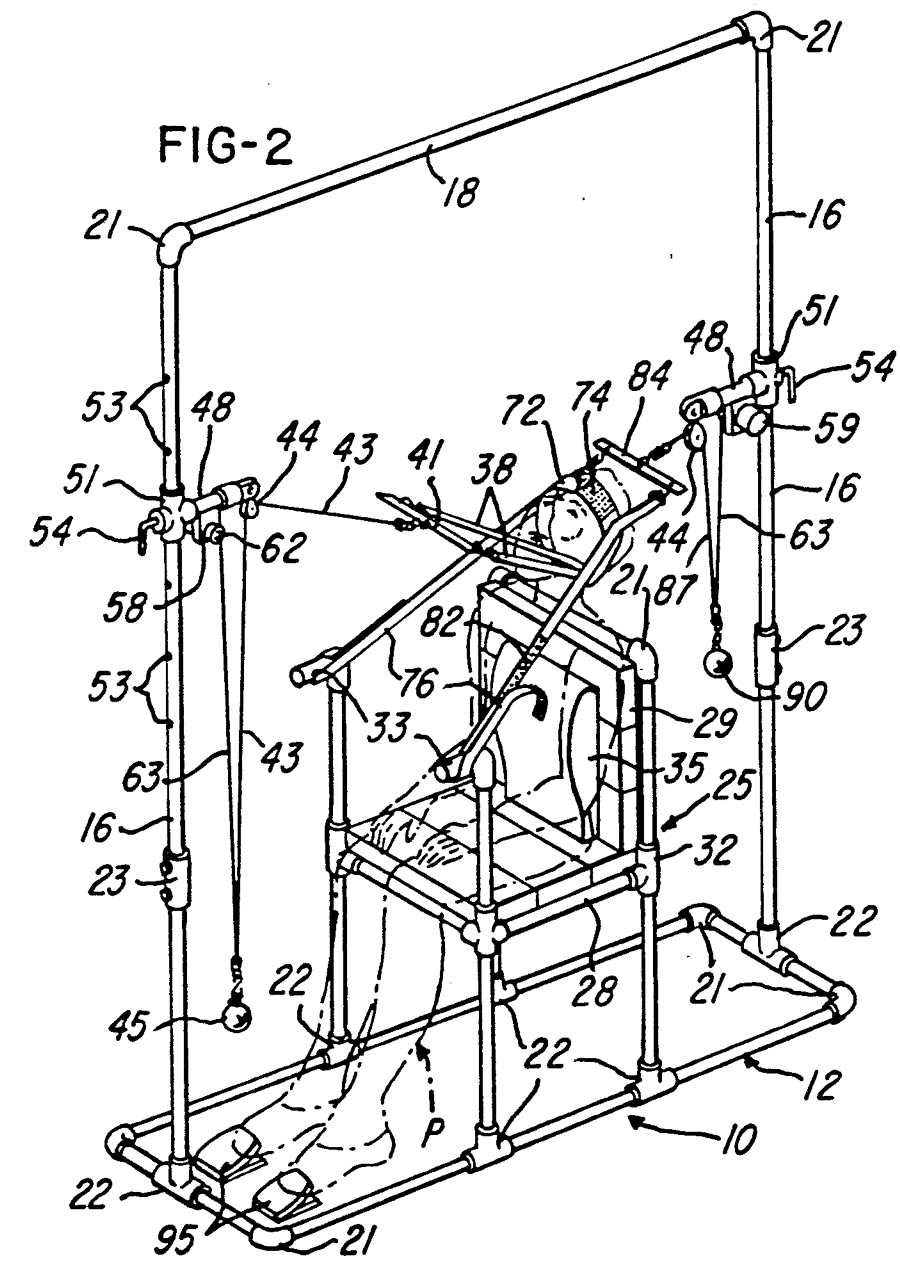
FIG. 2 is a perspective view of the apparatus shown in FIG. 1.

FIGS. 1 and 2 illustrate a traction apparatus 10 which includes a rigid frame 12 formed of precut sections of metal tubing. The frame includes a rectangular base section 14 and a pair of vertical sections or upright posts 16 rigidly connected by an overhead horizontal section 18. The tubular sections are coupled or connected together by right angle couplings or elbows 21, T-shaped couplings 22 and sleeve-type couplings 23, all of which carry set screws for rigidly connecting the tubular sections to form the rigid frame 12.

Four of the T-shaped couplings 22 within the base frame 14 support the legs of a chair 25 which is also formed by tubular metal sections connected together by couplings 21 and 22 for supporting a horizontal seat 28 and a vertical back 29 each formed of three rectangular members secured together by suitable means (not shown). A pair of right angle couplings or fittings 33 are attached to the upper ends of the front legs of the chair 25 and project forwardly as shown in FIG. 1.

A lumbar support pad 35 is mounted on the vertical back 29 of the chair 25 and is positioned to engage the middle of the lower back of a person P seated on the chair 25 in an upright position. An anterior or front fulcrum member or strap 38 extends around the person's neck and is placed at the level of the cervical spine that needs to be remodeled to a normal AP curve. The opposite ends of the strap 38 are connected to a cross bar 41, and a stainless steel cable 43 extends from the center of the cross bar 41 around a pulley 44 and then downwardly to a spherical weight 45, preferably within the range of ten to twenty pounds. An arm 48 projects inwardly from a T-shaped carriage or fitting 51 to support the pulley 44, and the fitting 51 is vertically slidable on the front frame section or post 16. A series of vertically spaced holes 53 are formed within each of the posts 16, and a spring-biased plunger or lock pin 54 is carried by the fitting 51 for releasably engaging one of the holes 53 to position the fitting 51 and arm 48 at different heights or elevations from the base 14 of the frame. As also shown in FIG. 1, the rear post 16 also supports a vertically adjustably arm 48 and corresponding pulley 44 gby means of sliding carriage or fitting 51 and releasable lock pin 54.

A power operated winch 58 is supported by each arm 48 and includes a reversible electric motor 59 connected through a gear reducer to a spool 62 on which is would a stainless steel cable 63. The lower end portion of the cable 63 depending from the winch 58 on the front post 16 is connected to the weight 45 and operates to lift the weight 45 so that it does not apply a force to the cable 43. One source of supply for the winch 58 is the Oriental Motor Company in Chicago, Ill.

The traction apparatus of the invention also incorporates a harness 70 which includes a headband 72 adapted to extend around the occiput or lower back part of the skull and also around the person's forehead. The headband 72 is firmly attached by means of an adjustable loop and hook fastener 74 commonly known as a VELCRO fastener. The harness 70 also includes a pair of flexible stabilizing straps 76 which are secured or stitched to the sides of the headband 74. The straps 76 have forward end portions which extend downwardly around the hook-shaped fittings 33 and attach upon themselves by means of VELCRO fasteners 82. The rearward end portions of the straps 76 are attached to a cross bar 84, and the center of the cross bar connects with a cable 87 which extends through the corresponding pulley 44 and then downwardly to another spherical weight preferably on the order of 10 lbs. In order to remove the weight 90 from pulling on the cable 87, the weight is elevated by the cable 63 depending from the winch 58 supported by the rear frame member or post 16. The operation of each of the winches 58 is controlled by the person P by actuating a corresponding pair of foot pedal switches 95 which control the corresponding reversible motors 59. The winches 58 may also be controlled by corresponding momentary hand operated switches mounted on the fittings 33.

Figure 3:
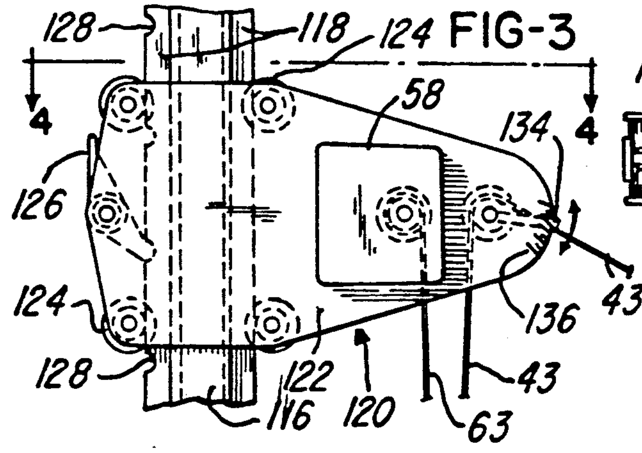
FIG. 3 is an enlarged elevational view of an adjustable force applying device constructed in accordance with a modification of the apparatus shown in FIGS. 1 and 2.
Figure 4:
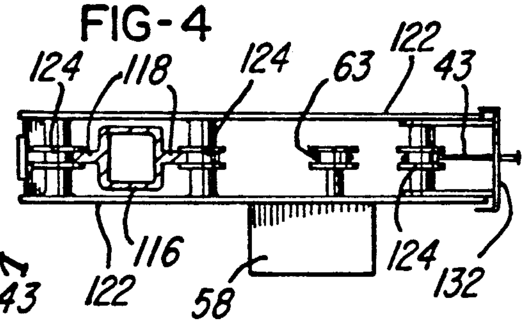
FIG. 4 is a view of the device taken generally on the line 4—4 of FIG. 3.

In place of the cylindrical metal tubing sections which couple together to form the frame 12 and the frame of the chair 25, the frames may be constructed of sections of square metal tubing which coupled together by means of internal coupling elements. One source of supply for the square metal tubing is AMCO Engineering Co. in Schiller Park, Ill. As shown in FIGS. 3 and 4, when the frame 12 is constructed of square metal tubing, the frame includes front and rear vertical members or posts 116 each of which has a pair of vertically extending and integrally extruded ribs or rails 118.

In place of each of the arms 48 and the sliding carriages or fittings 51, a carriage 120 (FIGS. 3 and 4) includes parallel spaced metal side plates 122 which are coupled together by a set of spacer tubes and rivets each of which supports a spool-like roller 124. As shown in FIG. 3, four of the rollers 124 of each carriage 120 engage the rails 118 on the post 116 and provide for shifting the carriage 120 vertically on the post 116. A spring loaded pivotal latch pawl 126 is also carried by the side plates 122 for selectively engaging the longitudinally spaced notches or recesses 128 formed within the adjacent rail 118 to position each of the carriages 120 at different elevations on the post 116.

Each of the carriages 120 carries one of the motor driven winches 158 for retracting and extending the corresponding cable 63, and another roller 124 (FIG. 4) forms a pulley for the cable 43. For selecting the angle at which the cable 43 extends downwardly to the fulcrum strap 38, an angle indicator 132 is supported for pivotal movement on the axis of the adjacent roller 124 and has pointed end portions 134 projecting adjacent the side plates 122 of the carriage 120. A protractor scale 136 is printed on the inner end portion of each side plate 122 and provides an indication of the angle at which the cable 43 extends from the horizontal downwardly to the neck strap 38. The indicator 132 rides on top of the cable 43 and moves with the cable 43 when the carriage 120 is moved upwardly or downwardly for selecting the optimum angle of applied force to the neck strap 38.

In operation of the traction apparatus 10, the person P is seated on the chair 25 in an upright position with the lumbar support pad 35 placed firmly in the small of the back. The front or anterior fulcrum strap 38 is placed at the level of the cervical spine that needs to be remodeled to a normal AP curve. The carriage 51 or 120 on the from post 16 or 116 is adjusted vertically to select the desired angle of pull by the cable 43 on the fulcrum strap 38. This angle of pull is selected based upon the reading of the extension lateral x-ray. Preferably, the angle is selected from the scale 136 on the carriage 120 and usually ranges between 10 degrees and 50 degrees.

The person then bends his head backwards to be generally horizontal with the floor and to set the normal AP curve. The harness 70 is then attached to the head by securing the headband 72 as shown in FIG. 1, and the straps 76 are connected to the fittings 33 with the aid of the adjustable VELCRO fasteners 82 and according to the person's height. The hooking of the straps 76 around the elbows 33 helps secure and stabilize the headband 72 and prevent it from slipping from the person's head. Preferably, the support carriage 48 or 120 on the rear post 16 or 116 is adjusted vertically so that the cable 87 pulls the harness 70 in a generally horizontal direction parallel to the floor. While attaching the strap 38 and harness 70, the selected weights 45 and 90 are retracted or lifted up to elevated positions by means of the winches 58. After the strap 38 and harness 70 are properly attached to the person, the person P operates the pedal or toe switches 95 so that the winches lower the cables 63 and weights 45 and 90 causing the weights 45 and 90 to apply the counter-stressing forces to the neck area for restoring the normal cervical curve.

From the drawings of the above description, it is apparent that counter-stressing traction apparatus constructed in accordance with the present invention, provides desirable features and advantages. For example, the apparatus applies a positive Z translation for pulling the cervical curve forwardly and also a positive Y translation for expanding the cervical spine upwardly by means of the anterior fulcrum strap 38. The angle of the upward pulling force by the anterior fulcrum strap may be determined by an extension x-ray taken with the person in only the headband harness 70. Also, the headband harness 70 with the stabilizing straps 76 are effective to position the person's head in a backward horizontal posture without introducing any stress on the facial muscles and/or temporal mandibular joints. Thus the apparatus of the invention applies corrective counter-stressing forces to the spine to restore optimum lordosis to the cervical spine by restoring the paraspinal soft tissues of muscles and ligaments to normal positions and lengths. As a result, the normal lateral curve of the spine is restored along with the normal function and health of the spine.

While the method and form of apparatus herein described constitutes a preferred embodiment of the invention, it is to be understood that the invention is not limited to the precise method and form of apparatus, and that changes may be made therein without departing from the scope and spirit of the invention as defined in the appended claims.

The invention having thus been described, the following is claimed:

1. Counter-stressing traction apparatus comprising means for supporting a person with a support for the thoracic and lumbar spine and to permit the person's cervical spine and skull to tilt backwardly relative to the person's torso, a headband for extending around the person's forehead and the lower back skull, means for retaining and stabilizing said headband on the person's head, a fulcrum member for extending around the person's neck, first means for applying a predetermined force for pulling forwardly on said fulcrum member relative to the person's torso, and second means for applying a predetermined force for pulling rearwardly on said headband and in a direction to tilt the person's head rearwardly around said fulcrum member for moving the person's cervical spine toward an optimum shape and alignment.

2. Apparatus as defined in claim 1 wherein said means for retaining and stabilizing said headband on a person's head comprise a pair of stabilizing straps having forward and rearward end portions connected by intermediate portions attached to said headband adjacent the sides of the person's head, and means for retaining said forward end portions of said straps in a position extending forwardly and downwardly in front of the person's torso.

3. Apparatus as defined in claim 1 wherein said fulcrum member comprises a flexible fulcrum strap extending around the person's neck and having forward end portions, and means for connecting said forward end portions to said first force applying means.

4. Apparatus as defined in claim 1 wherein said first and second force applying means comprise corresponding weight members connected to said fulcrum member and said headband by flexible cable-like members extending around corresponding rollers, and means for independently elevating said weight members from said cable-like members.

5. Apparatus as defined in claim 4 wherein said means for elevating said weight members comprise a set of motor driven winch units, and means for independently controlling said winch units.

6. Apparatus as defined in claim 1 wherein said means for supporting the person comprise a chair including a back portion having a lumbar support pad, said means for retaining and stabilizing said headband comprise a pair of flexible straps connected to said headband and extending downwardly and forwardly above the person seated on said chair, and means adjustably connecting said straps to said chair.

7. Apparatus as defined in claim 1 and including means for adjusting the angle at which said first force applying means pulls on said fulcrum member relative to the person's torso.

8. Apparatus as defined claim 1 and including means for vertically adjusting said second force applying means for obtaining a generally horizontal pulling force on said headband and for accommodating persons of different heights.

9. Apparatus as defined in claim 1 of and including a tubular metal frame having a base portion supporting a forward post and a rearward post, a chair connected to said frame for supporting the person in a seated position, and adjustable support means on said forward and rearward posts for supporting said first and second force applying means.

10. Counter-stressing traction apparatus comprising a frame connected to a chair for supporting a person, a pad within said chair for supporting the person's lumbar spine and to permit the person's cervical spine and skull to tilt backwardly over the top of the chair, a headband for extending around the person's forehead and the lower back skull, strap means connected to said headband and said chair for retaining and stabilizing said headband on the person's head, a fulcrum strap for extending around the person's neck, first means supported by said frame for applying a predetermined force for pulling forwardly on said fulcrum strap, and second means supported by said frame for applying a predetermined force for pulling rearwardly on said strap means and said headband and in a direction to tilt the person's head rearwardly around said fulcrum member for moving the person's cervical spine toward an optimum shape and alignment.

11. Apparatus as defined in claim 10 wherein said first and second force applying means comprise corresponding weight members connected to said fulcrum strap and said headband and strap means by flexible cable-like members extending around corresponding rollers, and means supported by said frame for independently elevating said weight members from said cable-like members.

12. Apparatus as defined in claim 11 wherein said means for elevating said weight members comprise a set of motor driven winch units, and means for independently controlling said winch units.

13. Apparatus as defined in claim 10 and including means supported by said frame for vertical adjustment for changing the angle at which said first force applying means pulls upwardly on said fulcrum strap relative to the person's torso.

14. Apparatus as defined claim 10 and including means supported by said frame for vertical adjustment for vertically adjusting said second force applying means to obtain a generally horizontal pulling force on said headband and for accommodating persons of different heights.

15. Apparatus as defined in claim 10 wherein said frame comprises a tubular metal frame having a base portion supporting a forward post and a rearward post, a tubular metal chair connected to said frame for supporting the person in a seated position, and vertically adjustable support means on said forward and rearward posts for supporting said first and second force applying means.

16. A method of remodeling a person's cervical spine for obtaining the optimum shape and alignment, comprising the steps of supporting the person with the person's head tilted backwards relative to the person's torso, extending a fulcrum member around the person's neck, attaching a headband around the person's forehead and the lower portion of the person's skull, pulling forwardly on the fulcrum member with a predetermined force and at a predetermined angle relative to the person's torso, and pulling rearwardly on the headband with a predetermined force for tilting the person's head rearwardly around the fulcrum member.

17. A method as defined in claim 16 wherein the step of supporting the person comprises seating the person on a chair with the person's torso generally vertical, and locating a lumbar support pad on the chair adjacent the lower portion of the person's back.

18. A method as defined in claim 17 and including the step of stabilizing the headband extending around the person's head by extending adjustable straps from the sides of the headband forwardly and downwardly to the chair, and connecting the straps to the chair.

* * * * *